(12) United States Patent
Mitra

(10) Patent No.: US 7,147,695 B2
(45) Date of Patent: Dec. 12, 2006

(54) MICROFABRICATED MICROCONCENTRATOR FOR SENSORS AND GAS CHROMATOGRAPHY

(75) Inventor: Somenath Mitra, Bridgewater, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 263 days.

(21) Appl. No.: 10/735,988

(22) Filed: Dec. 15, 2003

(65) Prior Publication Data

US 2004/0194628 A1 Oct. 7, 2004

Related U.S. Application Data

(60) Provisional application No. 60/433,475, filed on Dec. 13, 2002.

(51) Int. Cl.
*B01D 53/04* (2006.01)

(52) U.S. Cl. .................. 96/101; 96/102; 96/143; 96/146; 95/82; 95/87; 95/115; 73/23.35; 73/23.41; 205/640; 205/666; 204/192.1

(58) Field of Classification Search .............. 73/23.35, 73/23.39, 23.41; 95/82, 87, 89, 115, 120, 95/126, 101–107, 143, 146; 203/640, 666; 204/192.1
See application file for complete search history.

(56) References Cited

U.S. PATENT DOCUMENTS

| | | | | |
|---|---|---|---|---|
| 3,538,744 A | * | 11/1970 | Karasek | 73/23.39 |
| 4,599,095 A | * | 7/1986 | Barnes et al. | 96/146 |
| 4,726,822 A | * | 2/1988 | Cates et al. | 96/101 |
| 4,935,040 A | * | 6/1990 | Goedert | 73/23.22 |
| 5,087,275 A | * | 2/1992 | Pribat et al. | 96/101 |
| 5,376,252 A | * | 12/1994 | Ekstrom et al. | 204/603 |
| 5,658,413 A | * | 8/1997 | Kaltenbach et al. | 156/272.8 |
| 5,997,708 A | * | 12/1999 | Craig | 204/601 |
| 6,068,684 A | * | 5/2000 | Overton | 96/104 |
| 6,068,780 A | * | 5/2000 | Yu | 216/10 |
| 6,074,725 A | * | 6/2000 | Kennedy | 428/188 |
| 6,503,298 B1 | * | 1/2003 | Monzyk et al. | 95/96 |
| 6,508,862 B1 | * | 1/2003 | Tonkovich et al. | 95/106 |
| 6,527,835 B1 | * | 3/2003 | Manginell et al. | 96/102 |

(Continued)

FOREIGN PATENT DOCUMENTS

JP 61-142462 A * 6/1986

(Continued)

OTHER PUBLICATIONS

A. Friedberger et al.; A Versatile And Modularizable Micromachining Process For The Fabrication Of Thermal Microsensors and Microactuators; Journal of Micromechanics and Microengineering; Sep. 7, 2001; pp. 623-629.

(Continued)

*Primary Examiner*—Jason M. Greene
(74) *Attorney, Agent, or Firm*—Kaplan, Gibman, Gibson & Dernier

(57) ABSTRACT

Devices for enhancing the sensitivity of a microsensor or any other micro device by providing on-line preconcentration. Microconcentrators that can be integrated with a sensor or a micromachined GC to enhance the signal to noise ratio can include a miniaturized sorbent trap fabricated on a microchip. The microconcentrator can be made on a silicon substrate so that a sensor can be integrated on the same chip. The microconcentrator is composed of at least one microchannel lined with a microheater for in-situ heating. Preconcentration may be achieved on a thin-film polymeric layer deposited above the heater in the microchannel. Rapid heating by the channel heater generates a "desorption pulse" to be injected into a detector or a sensor.

31 Claims, 9 Drawing Sheets

U.S. PATENT DOCUMENTS

| | | | |
|---|---|---|---|
| 6,527,890 B1 * | 3/2003 | Briscoe et al. ............ | 156/89.11 |
| 6,663,697 B1 * | 12/2003 | Kottenstette et al. .......... | 96/101 |
| 6,666,907 B1 * | 12/2003 | Manginell et al. .............. | 95/87 |
| 6,670,024 B1 * | 12/2003 | Yu .............................. | 428/209 |
| 6,699,392 B1 * | 3/2004 | Manginell et al. ........... | 210/656 |
| 6,706,091 B1 * | 3/2004 | Robinson et al. ............... | 95/87 |
| 6,792,794 B1 * | 9/2004 | Bonne et al. ............... | 73/25.01 |
| 2002/0178785 A1 * | 12/2002 | Lo et al. ..................... | 73/23.41 |
| 2003/0145725 A1 * | 8/2003 | Hastings et al. ................ | 95/87 |
| 2003/0233862 A1 * | 12/2003 | Wise et al. ................. | 73/23.39 |
| 2004/0255643 A1 * | 12/2004 | Wise et al. ................. | 73/23.39 |
| 2005/0045030 A1 * | 3/2005 | Tonkovich et al. ............. | 95/90 |

FOREIGN PATENT DOCUMENTS

| | | | |
|---|---|---|---|
| JP | 61-233365 A | * | 10/1986 |
| JP | 61-288154 A | * | 12/1986 |
| JP | 62-103569 A | * | 5/1987 |

OTHER PUBLICATIONS

Ivonne Schneegaβ, et al.; Miniaturized Flow-Through PCR With Different Template Types In A Silicon Chip Thermocycler; Institute of Physical High Technology; Aug. 9, 2001; pp. 1-16.

John S. Suehle, et al.; Tin Oxide Gas Sensor Fabricated Using CMOS Micro-Hotplates and *In-Situ* Processing; IEEE Electron Device Letters; vol. 14, No. 3, Mar. 1993; pp. 118-120.

Yukikio Hosoda et al.; Fabrication And Applications Of Polymer-Based Microchannel-Heater Chip As Microreactor; Micro Total Analysis Systems, 2002.

J. Laconte et al.; SOI CMOS Compatible Low-Power Microheater Optimization And Fabrication For Smart Gas Sensor Implementations; IEEE International Conference on Sensors; 2002.

Gwiy-Sang Chung et al.; The Fabrication Of Micro-Heaters With Low-Power Consumption Using SOI And Trench Structures; Metals and Materials International; 2002.

V. Guarnieri et al.; Low-Power Silicon Microheaters On A Thin Dielectric Membrane With Thick-Film Sensing Layer For Gas Sensor Applications; Microelectronics, Microsystems and Nanotechnology; 2000.

Yaowu Mo et al.; Low-Voltage And Low-Power Optimization Of Micro-Heater And Its On-Chip Drive Circuitry For Gas Sensor Array; Sensors and Actuators, A: Physical, 2002.

W. C. Tian et al.; Freestanding Microheaters In Si With High Aspect Ratio Microstructures; Journal of Vacuum Science & Technology, B; Microelectronics and Nanometer Structures; 2002.

Tailian Chen et al.; Coalescence Of Bubbles In Nucleate Boiling On Microheaters; International Journal of Heat and Mass Transfer; 2002.

A. V. Korlyakov et al.; Infrared Microradiator Based On SiC-on Isulator Thin-Film Structures; Journal of Optical Technology; 2001.

Y. Mo. et al.; Micro-Machined Gas Senor Array Based On Metal Film Micro-Heater; Sensors and Actuators, B: Chemical; 2001.

Gwiy-Sang Chung et al.; Fabrication of Pt Microheater Using Aluminum Oxide As A Medium Layer And Its Characteristics; Sensors and Materials; 1998.

Carole Rossi et al.; Realization And Performance Of Thin SiO2/SiNx Membrane For Microheater Application; Sensors and Actuators, A: Physical; 1998.

* cited by examiner

MICROFABRICATED MICROCONCENTRATOR FOR SENSORS AND GAS CHROMATOGRAPHY

RELATED APPLICATIONS

This application claims the benefit of U.S. Provisional Application No. 60/433,475, filed Dec. 13, 2002, entitled "Microfabricated Microconcentrator for Sensor and Chromatography," the entirety of which is incorporated herein by reference.

FIELD OF THE INVENTION

The present invention relates to microconcentrators, specifically, microconcentrators for devices such as sensors and gas chromatographs.

BACKGROUND OF THE INVENTION

Environmental monitoring requires the measurements of pollutants at trace concentrations (ppm to ppt), because even at these levels they pose a threat to human health and to the environment. A variety of conventional laboratory based analytical techniques are used for pollution monitoring. Currently, gas chromatographs, mass spectrometers and Fourier transform infrared spectrometers (FTIR) are the most commonly used instruments. These techniques have excellent merits in terms of sensitivity, detection limit and other performance characteristics. However, they are relatively large, expensive and do not lend themselves to easy portability.

The increasing needs for inexpensive, small monitoring devices have added new impetus to miniaturize analysis systems. It is well known that miniaturization offers functional and economic benefits such as the reduction in sample size, decrease in reagent consumption and inexpensive mass production. Advancements in thin-film technologies have expanded the range of possible microsensor designs. On the other hand, micromachining processes, particularly anisotropic and plasma etching, and the sacrificial layer method make possible the construction of a variety of three-dimensional structures. It is feasible to employ these methods to produce sophisticated, low power integrated sensing systems at a modest cost. The high degree of reproducibility and the relatively small size of these devices enhance both performance and the potential for practical applications.

A few types of microsensors have been developed to date. Tin-oxide-based sensors have been widely used in gas sensing. An important environmental application is the detection of low concentration toxic gases (i.e., CO, $NO_2$, $O_3$ etc.). $SnO_2$ films are commonly used as gas sensors due to their high sensitivity to different gases, low production cost, and the ease of use. Surface acoustic wave (SAW) sensors are another widely used class of highly sensitive environmental sensors. A coated SAW device acts as a chemical sensor by adsorbing analytes on its surface. A mass loading on the surface results in a change in propagation velocity and a corresponding phase shift. Schottky-diode-type sensors have also been used in gas sensing, in which, when an analyte diffuses towards the interface between the metal and the insulting layers of a diode, the height of the Schottky barrier diminishes, leading to a change in either the forward voltage or the reverse current.

Chemical species can be detected using electrochemical sensors. An example of a solid electrolyte electrochemical sensor is the $ZrO_2$—based high-temperature oxygen sensor. This sensor is operated at 650° C. to ensure the ionic conductivity of $ZrO_2$.

Micromachined gas chromatographs have also been developed. GC columns have been etched on silicon, and diaphragm based valves have been developed as GC injectors. Micromachined thermal conductivity detectors have been successfully made, and are commercially available.

In principle, sensors and other micro devices can provide real-time (or near real-time), on-line measurements. It is desirable that they be completely automated, and not require additional chemical reagents or sample preconditioning. However, the absence of memory effects, high sensitivity, selectivity, reproducibility, short response time and long-term stability are prerequisite for their real-world applicability. The limited success of microsensors are due to the inability to meet some of these requirements. In trace analysis, such as in environmental monitoring, the biggest drawback has been the low sensitivity, and the high detection limits of the sensors.

One way to enhance sensitivity in any measurement is to provide some kind of preconcentration. The key component in trace analysis is the concentration step where the analytes are accumulated before the analysis. Sorbent trapping in air sampling, solid phase extraction and SPME are common examples of preconcentration. This allows a larger amount of analyte to be concentrated and then released into a detection device. Larger sample throughput in terms of the mass of analyte per unit time results in a higher signal to noise ratio.

A small sorbent trap known as a microtrap has been employed as a concentration plus injection device for continuous monitoring of organics in gas streams by gas chromatography, mass spectrometry, or by a non-methane organic carbon (NMOC) analyzer. Sample passes continuously through the microtrap, and periodic electrical heating releases the adsorbed analytes as a "concentration pulse", which serves as an injection for the detection system. Its small size allows it to be cycled at high frequency, and the preconcentration effect allows ppb level detection.

However, as yet there has been no way to provide a preconcentration microdevice that may be employed in conjunction with a microsensor.

SUMMARY OF THE INVENTION

The present invention provides a device for enhancing the sensitivity of a microsensor (or any other micro device) by providing on-line preconcentration. The invention provides a micromachined concentrator (hereinafter referred to as the microconcentrator) on a silicon substrate, that can be integrated with a sensor or a micromachined GC to enhance the signal to noise ratio. The present invention comprises a microconcentrator comprising a miniaturized sorbent trap fabricated on a microchip. In a preferred embodiment the microconcentrator is made on a silicon substrate so that a sensor or micromachined GC can be integrated on the same chip. In accordance with the invention, in practice the microconcentrator is put on-line with a sample stream and may be operated at a fixed frequency. A preferred embodiment of the microconcentrator is composed of at least one microchannel etched in silicon. The channel is lined with a microheater for in-situ heating. In a most preferred embodiment preconcentration is done on a thin-film polymeric layer deposited above the heater in the channel. Rapid heating by the channel heater generates a "desorption pulse" to be injected into a detector, or, a sensor. The preconcentration effect provided by the microconcentrators of the present invention were found to enhance sensitivity, provide stable response, and exhibit good precision.

In another embodiment the microconcentrator of the present invention is concentrator-injector for a gas chromatograph.

OBJECTS OF THE INVENTION

It is therefore an object of the present invention to provide a microconcentrator that can be used with any sensor, sensor array, electronic nose, micro-GC, two dimensional GC, or comprehensive two dimensional GC.

It is a further object of the present invention to provide a microconcentrator that is an integral part of a detector.

It is a further object of the present invention to provide a microconcentrator that can be used in conjunction with sensors used in the field of homeland defense such as sensors for explosives and chemical warfare agents, and in the field of environmental sensing.

It is yet a further object of the present invention to provide a microconcentrator that can be used with miniature as well as large devices such as gas chromatographs, mass spectrometers and Fourier transform infrared spectrometers (FTIR).

It is yet a further object of the present invention to provide a microconcentrator capable of serving as a sorbent trap in analytical instruments such as purge and trap, solid phase microextraction and the like.

It is still a further object of the present invention to provide a microconcentrator that modulates concentration and increases sensitivity by analyte preconcentration.

It is a further object of the present invention to provide a microconcentrator in which the sorbent material may be selected from a polymer film, sorbent particles and carbon based materials.

It is still a further object of the present invention to provide a microconcentrator that can be used for organics, inorganics, gases, volatile organics, chemical warfare agents, vapors, and liquids.

It is still a further object of the present invention to provide a microconcentrator that can be used as a GC injector.

It is still a further object of the present invention to provide a microconcentrator in which the preconcentration effect provides enhanced sensitivity, stable response, and good precision.

These and other objects will be apparent to those having skill in the art.

DETAILED DESCRIPTION OF THE PREFERRED EMBODIMENT

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to "one embodiment" or "an embodiment" means that a particular feature, structure or characteristic described in connection with the embodiment is included in at least one embodiment of the invention. The appearances of the phrase "in one embodiment" in various places in the specification are not necessarily all referring to the same embodiment.

The teachings of U.S. Provisional Application No. 60/433,475, filed Dec. 13, 2002, entitled "Micromachined Heater for Microfluidic Devices," and related U.S. patent application Ser. No. 10/735,989, and "A microfabricated microconcentrator for sensors and gas chromatography, M. Kim and S. Mitra, Journal of Chromatography A, 996 (2003) 1–11 are incorporated herein in their entirety by reference.

Now referring to FIGS. 1A–1G a preferred embodiment of a method for preparing a microconcentrator 2 according to the present invention discloses step-by-step processing of the wafer 10 and its cross-sectional view after each step. Wafer 10 may comprise a commercially available material commonly used for photolithographic fabrication such as but not limited to quartz, borosilicate glass or a suitable polymer known in the art. Quartz is a desirable material in electrophoresis because it is a good electrical insulator and is transparent to the UV required for absorbance and fluorescence detection. Quartz substrates also generate high electroosmotic flow rates and have favorable surface characteristics after fabrication by etching. Silicon is also desirable because it is possible to embed both fluid-control and fluid detection by integrated circuits on one substrate. By way of comparison the typical fluidic devices such as microreactors and microfluidic capillaries are 2–3 cm$^2$ in size, and are made of silicon, glass, quartz, or plastic that are either etched, microimprinted or molded. The etched channels and chambers are usually covered with Pyrex, glass or silicon to contain the sample and the reagent. In a preferred embodiment wafer 10 comprises an oriented, p-typed (boron doped), single side polished silicon wafers with a thickness of 575 μm and a resistivity of 10–25 Ω-cm.

Figure 1A:
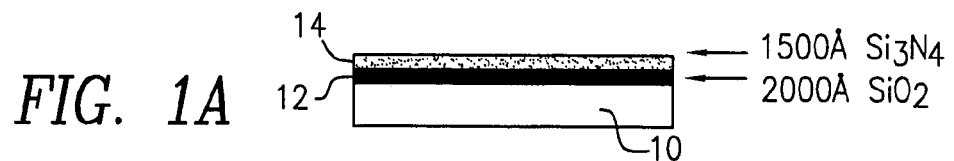
FIGS. 1A–1G reflect a step-by-step graphical depiction, in cross-section, of a preferred embodiment of a microconcentrator fabricated in accordance with a method of the present invention.
Figure 1B:
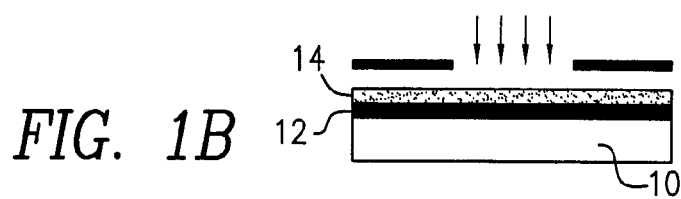
Figure 1C:
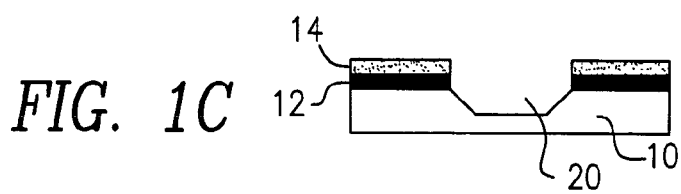

Now referring to FIG. 1A a wafer 10 is preferably prepared by steam oxidation to grow the oxide layer ($SiO_2$) 12 to a thickness of about 2000 Å with standard deviation of +/−32 Å. This step is followed by LPCVD (low pressure chemical vapor deposition) to deposit the silicon nitride layer ($Si_3N_4$) 14 in a thickness of about 1550 Å with standard deviation of +/−18 Å. Now referring to FIG. 1B the wafer 10 is patterned using standard UV lithography. Preferably the patterned wafers are etched using Reactive Ion Etching (RIE), a combination of plasma etching and ion beam removal that has the major advantage of etching the silicon dioxide over the silicon layers. Now referring to FIG. 1C the wafer is next anisotropically etched with potassium hydroxide. In one embodiment this step uses KOH 45% by volume and is performed at 95° C. The etch rate depends upon the doping and crystal orientation of the silicon, and the type/temperature of KOH solution used. Channel 20 is formed by this step. Now referring to FIGS. 1C–1G, etching the oriented silicon wafers in KOH typically produces wells with angled sidewalls. Where the wafer substrate 10 is oriented, chemical wet etching will produce the channel 20 anisotropically with low aspect ratio. As a result, the channel 20 geometry is trapezoidal as shown in FIG. 1C. However, channels 20 of any shape or size may be employed depending on the application as will be apparent to one having skill in the art. The configuration of channel 20 may be fabricated with varying widths, depths and lengths depending on the application, with widths between 50 to 456 μm being preferred, depths between 35 and 350 μm being preferred and length between 6 and 19 cm being preferred. The separation distance between the channels may be varied to fit the space in which the microconcentrator 2 will be located.

Figure 1D:
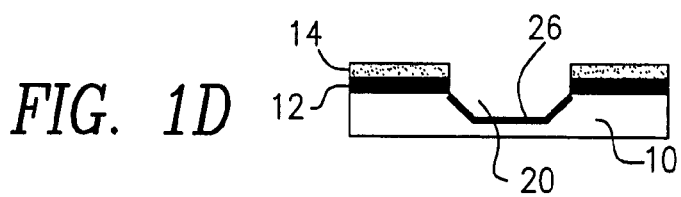

Now referring to FIG. 1D in a preferred embodiment a resistive layer 26 is deposited in channel 20 to provide a heating element. In FIG. 1D deposition of a resistive layer 26 such as but not limited to a conductor such as metal in the channel 20 by sputtering is performed. Resistive layer 26 may be any suitable conducting material such as but not limited to iron, copper, aluminum, chromium, gold, silver, platinum or the like, alloys thereof, composites of organic conducting polymers and metals and the like. Resistive layer 26 may be a suitable organic conducting polymer. In a most preferred embodiment the resistive layer 26 is an aluminum alloy comprising 99% aluminum, the rest being silicon and copper. Silicon-aluminum alloys prevent the silicon from reacting with the deposited aluminum, which could cause spiking or shorted circuits.

Optionally, ion implantation is performed to deposit the resistive layer 26 wherein dopant atoms are ionized, formed into a beam, and swept across the wafer 10. The bombarding atoms enter the wafer substrate 10 and come to rest below the surface of the wafer 10. The dopant employed is preferably boron.

Figure 1E:
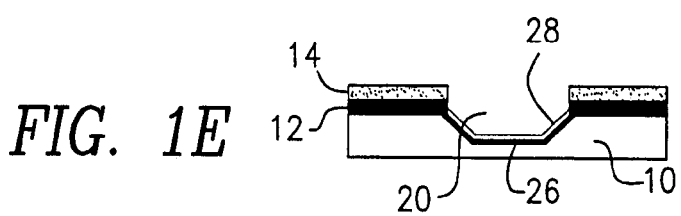

Now referring to FIG. 1E, optionally a substrate 28 such as but not limited to glass, ceramic or a suitable polymer is applied in channel 20 because organic polymers employed as the absorbing film in accordance with the present invention have low adhesivity to silicon and metal. In a preferred embodiment substrate 28 is a layer of spin on glass (SOG) applied in channel 20. It is expected that in many applications, it would be desirable that channel 20 would be coated with some other material such as glass or polymer. Glass-based surfaces also provide the potential of chemical modification using organosilanes. Hence, in a preferred embodiment, a SOG layer 28 is applied on the channel 20. The thickness of the SOG layer 28 may be controlled by the speed of the spinner applicator. For example, to achieve a glass thickness of 1 μm on a 6" wafer, 4 ml of SOG may be applied at 2000 RPM for a period of 2.0 seconds. Variations of this method may be employed to vary thickness of the SOG layer 28. The application step is preferably followed by a baking step such as hard plate baking at 80° C., 150° C. and 250° C. for 40 seconds each. Preferably a curing step is employed wherein the wafer 10 is cured in a furnace, optimally at 425° C. for 60 minutes for a 1 μm SOG layer. Variations in temperature and time may be necessary depending on the equipment used, wafer composition, SOG thickness, resistive layer type and the like as will be apparent to one having skill in the art.

Figure 1F:
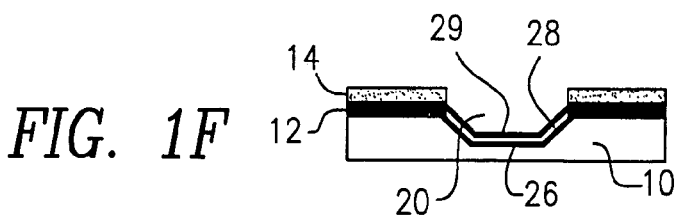

Now referring to FIG. 1F an absorbing layer 29 is formed in channel 20. Thin films of commercially available gas chromatography stationary phase such as OV17 (50% poly-methyl-50% phenyl-phase, from Supelco Inc., Supelco Park, Pa.) are deposited on the channel 20 of microconcentrator 2 preferably by spin coating. For example, layer 29 may be applied by spin coating at 2000 rpm for 20 seconds. The thickness of the polymeric layer may be varied by adjusting spin-coating conditions as is known to those skilled in the art. The coated wafer is then baked in an oven, preferably at 120° C. for 48 hours. Absorbing layer may in an alternate embodiment comprise other well-known absorbent material known to those of skill in the art, such as but not limited to suitable chemical agents, carbon and the like.

Figure 1G:
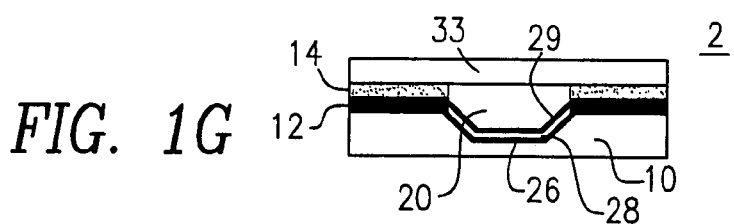

Now referring to FIG. 1G a sealing layer 33, such as but not limited to glass, quartz glass, silicon, a substrate with or without a further microchannel, or another suitable material, is applied over channel 20. Bonding of the glass layer to the patterned silicon of the microconcentrator may be carried out using any suitable adhesive such as but not limited to WaferGrip® (Dynatex, Santa Rosa, Calif.). WaferGrip is an advanced composite film adhesive engineered to bond wafers and other substrates during dicing, grinding, lapping and polishing. WaferGrip is heat activated and is rated by the manufacturer to have uniform thickness. In a preferred embodiment the adhesive layer of WaferGrip is compressed on the substrate under vacuum using a wafer bonder to provide a leak proof device. FIG. 1G shows the cross section view of the microconcentrator of the present invention prepared according to one embodiment of the present invention.

Other embodiments of the heating element of the microconcentrator of the present invention may be provided. For example a micro-scale separate heating element placed within the channel, or an external heating element such as a laser pulse may be employed as will be apparent to one of skill in the art in view of the present invention.

The microconcentrator 2 of the present invention provides a general-purpose device that can be used with any sensor, sensor array or detector, either separately or as an integral part thereof. The present microconcentrator can be used for organics, inorganics, gases, volatile organics, chemical warfare agents, vapors, and liquids. For example, the microconcentrator can be used as a modulator in two-dimensional chromatography and comprehensive two-dimensional chromatography. The microconcentrator can be employed as an integral part of a detector. Important applications of the present microconcentrator include use in conjunction with sensors used in the field of homeland defense such as sensors for explosives and chemical warfare agents, and in the field of environmental sensing. The present microconcentrator can be used with miniature as well as large devices such as gas chromatographs, mass spectrometers and Fourier transform infrared spectrometers (FTIR). The microconcentrator can also be used as a GC injector. The present␣microconcentrator is further capable of serving as a sorbent trap in analytical instruments such as purge and trap, solid phase microextraction and the like.

Figure 2:
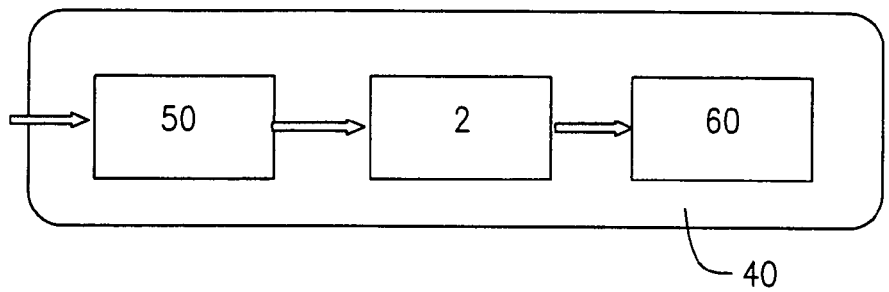
FIG. 2 is a schematic diagram of an embodiment of the present invention.
Figure 3:
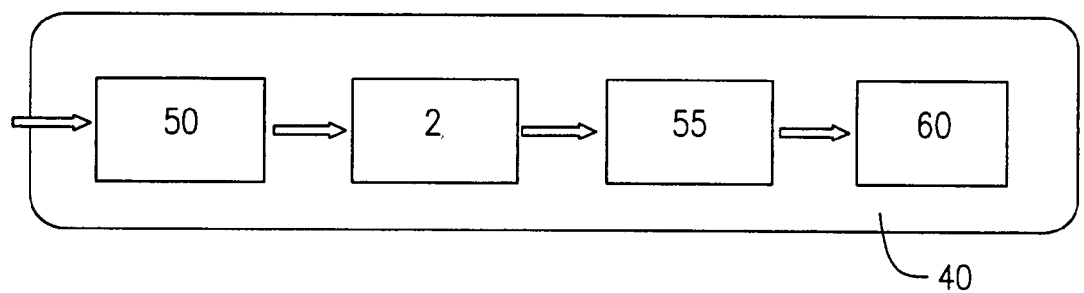
FIG. 3 is a schematic diagram of an alternate embodiment of the present invention

Now referring to the schematic of FIG. 2, in one embodiment the microconcentrator 2 is integrated on a silicon chip 40 with a micropump 50 and sensor or sensor array 60. The arrows refer to the direction in which a sample is injected and flows through the system. Now referring to the schematic of FIG. 3, in another embodiment the microconcentrator is integrated on a silicon chip with a micropump 50, GC separator 55 and sensor or sensor array 60, the arrows indicating sample flow through the system.

Figure 4:
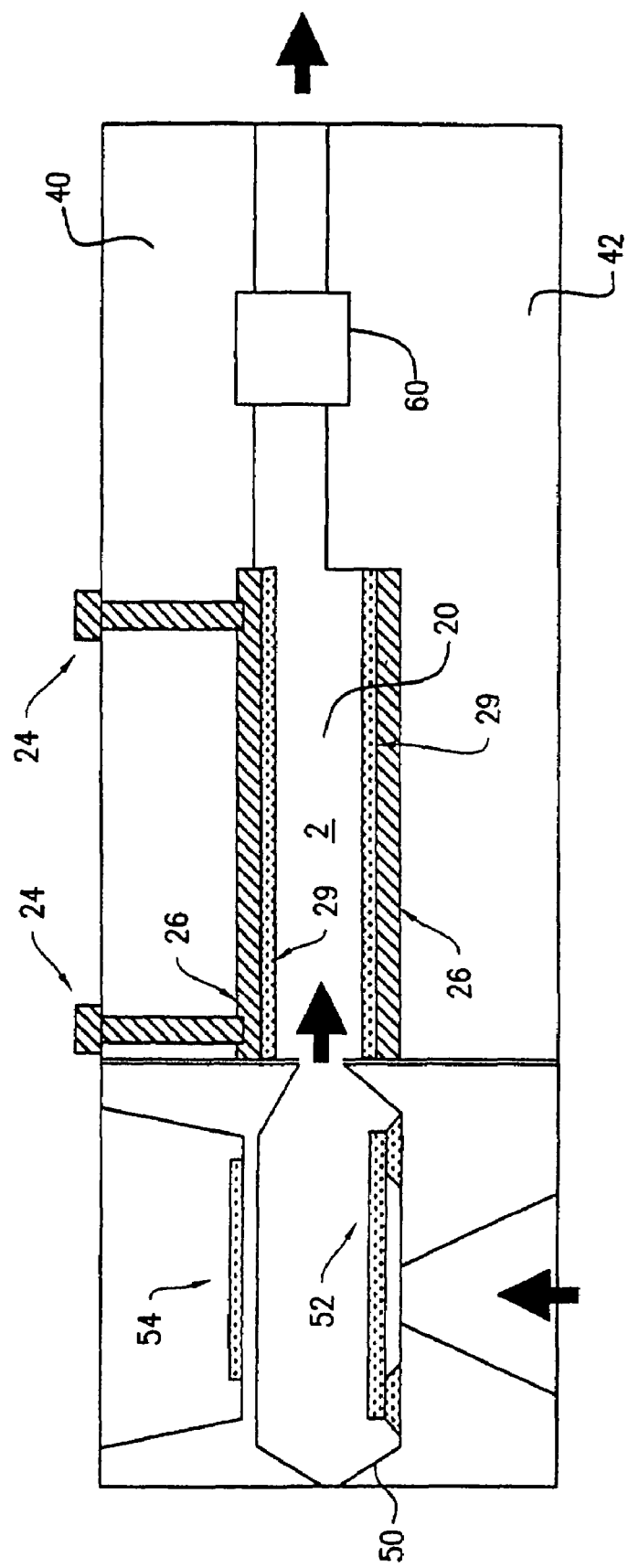
FIG. 4 is a side view of a cross section of a preferred embodiment of an integrated microconcentrator and sensor according to the present invention.

Now referring to FIG. 4, a side view of a cross section of a preferred embodiment of an integrated microconcentrator and sensor according to the present invention is shown. Microconcentrator 2 essentially comprises a top wafer 40 and bottom wafer 42 having microchannels formed thereon, preferably mirror images of each other, bonded together to form a closed microchannel 20. The microconcentrator 2 is integrated on a silicon chip 40 with a micropump 50 and sensor or sensor array 60. Microconcentrator 2 comprises a heating element consisting of resistive layers 26 with or without a substrate such as but not limited to SOG; channel 20; and absorbing layers 29. In this embodiment the microconcentrator 2 may comprise one or more resistive layer 26 and/or absorbing layer 29. Contacts 24 are employed for heating the heating element of the microconcentrator 2. Micropump 50 comprises inlet valve 52 and electrically actuated diaphragm 54 for micropumping. This embodiment is preferably employed for air monitoring applications wherein active pumping is used. The arrows refer to the direction in which a sample is injected and flows through the system.

Experiment 1

Figure 5:
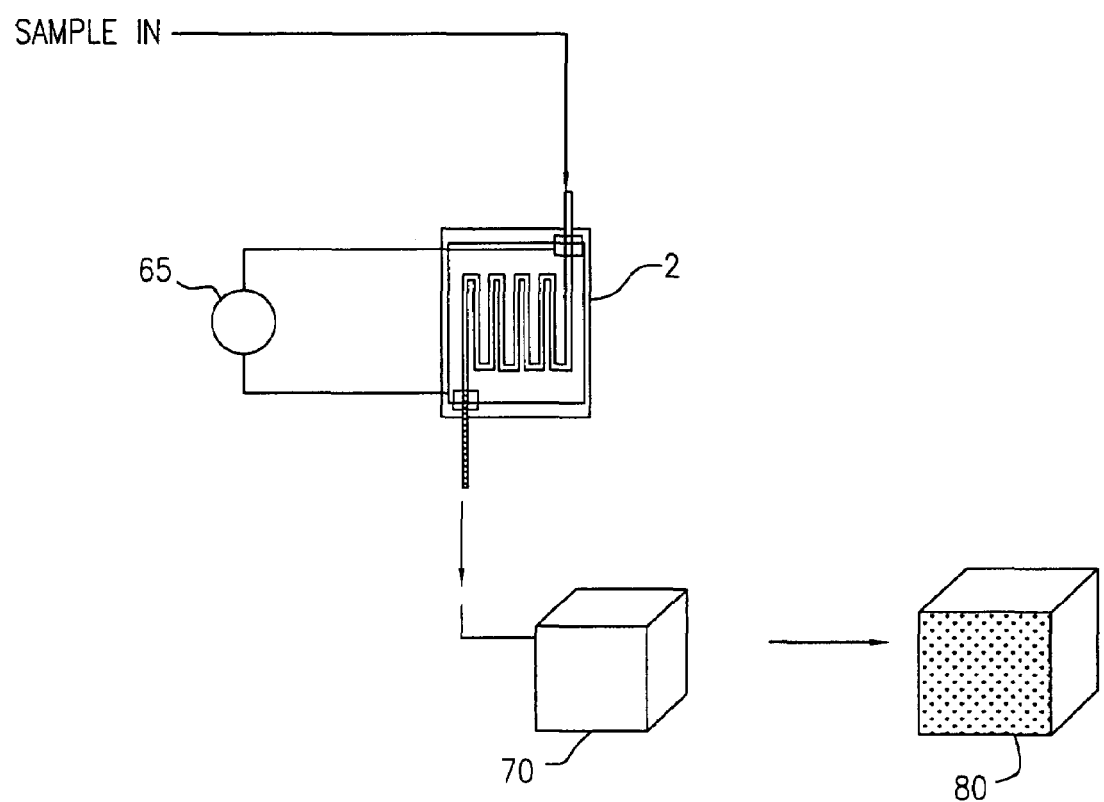
FIG. 5 is a schematic diagram of an embodiment according to the present invention.

Now referring to FIG. 5, a microconcentrator 2 in accordance with the present invention was employed in conjunction with a pulse heater 65, a conventional flame ionization detector (FID) 70, in this case a SRI Instrument Model 8600/9300 portable GC equipped with a FID and a computer 80 for data acquisition. The microconcentrator 2 was cooled by placing it over an ice pack. A commercially available capillary column such as a 0.53 mm ID, 30 m long capillary column (DB-624,J&W Scientific) was employed in some tests. Repeat injections were made under isothermal conditions to generate a series of chromatograms. Standard gases such as air, nitrogen, and hydrogen were purchased from Matheson Gas Co., NJ. Nitrogen was used as the carrier gas, and the flow rate was 7 ml/min. Data acquisition was carried out using the Peaksimple Data System supplied by SRI Instruments. Calibration, qualitative/quantitative analysis, documentation of analytical results, and report output were handled by this system.

The standard gaseous stream was generated using the diffusion tube method, and typical concentrations were between 5 and 20 ppm$_v$. Steady streams of benzene, toluene or ethyl benzene were generated by diffusing a controlled amount of the analyte from the diffusion capillary into a flow of $N_2$. The organic vapors were adsorbed by the microconcentrator 2. The preconcentration was done on a thin-film polymeric layer 29 deposited in the channel 20 as shown in FIG. 1G. A pulse of electric current (AC) was applied to the microconcentrator 2 at predetermined intervals to desorb the trapped organics. Duration of the pulse was between 1 to 3 seconds. Rapid heating of the conductive layer 26 caused the "desorption pulse" to be injected into the detector 70. A microprocessor-based controller was used to control the interval and the duration of the electrical pulses to the heater 65.

Heating Characteristics of the Microchannel Heater

Figure 6:
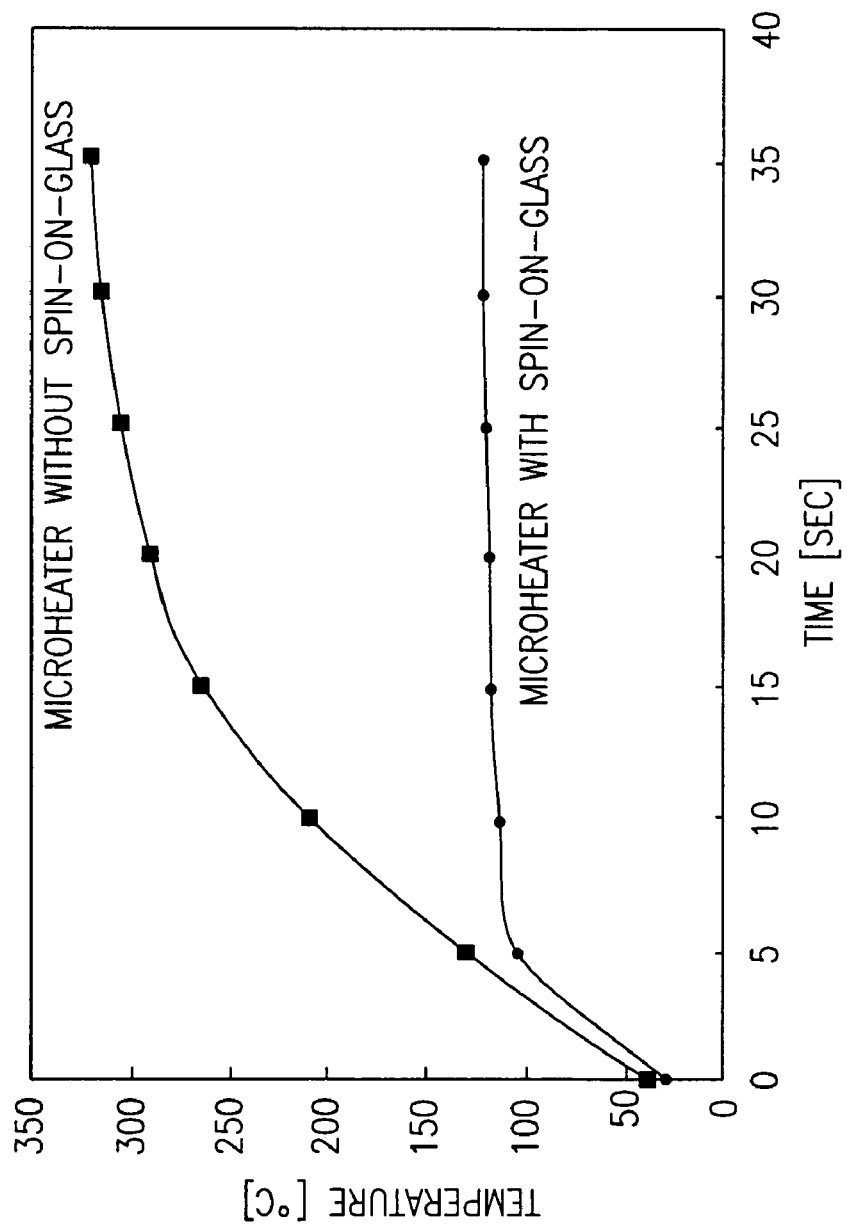
FIG. 6 is a graphical representation of temperature characteristics of a heater embedded in a microconcentrator according to the present invention.

A key component in the preferred embodiment of the microconcentrator of the present invention is the heating element. The heating characteristics of the channel heater were studied. The temperature of the microchannel 20 was measured using a 50 μm thermocouple. A typical temperature profile as a function of time is plotted in FIG. 6. The temperature depended upon several factors such as heater design, applied voltage etc. For the heater presented here, temperature as high as 200° C. could be reached in less than 10 seconds. The SOG provided a resistance to heat transfer and the maximum temperature reduced to 120° C. Depending on the response of the thermocouple the real heat-up rate could be somewhat higher. Detailed heating characteristics of such thin-film heater have been presented elsewhere, and the heater stability during multiple cycling has been demonstrated in M. Kim, S. Kishore, D. Misra and S. Mitra, In Review, Lab on a Chip, (2003), incorporated herein by reference in its entirety. The heated channel 20 in this study had a width of 450 μm, depth of 300 μm, and the total length was 16 cm.

Experiment 2—On-Line Microconcentrator

Figure 7:
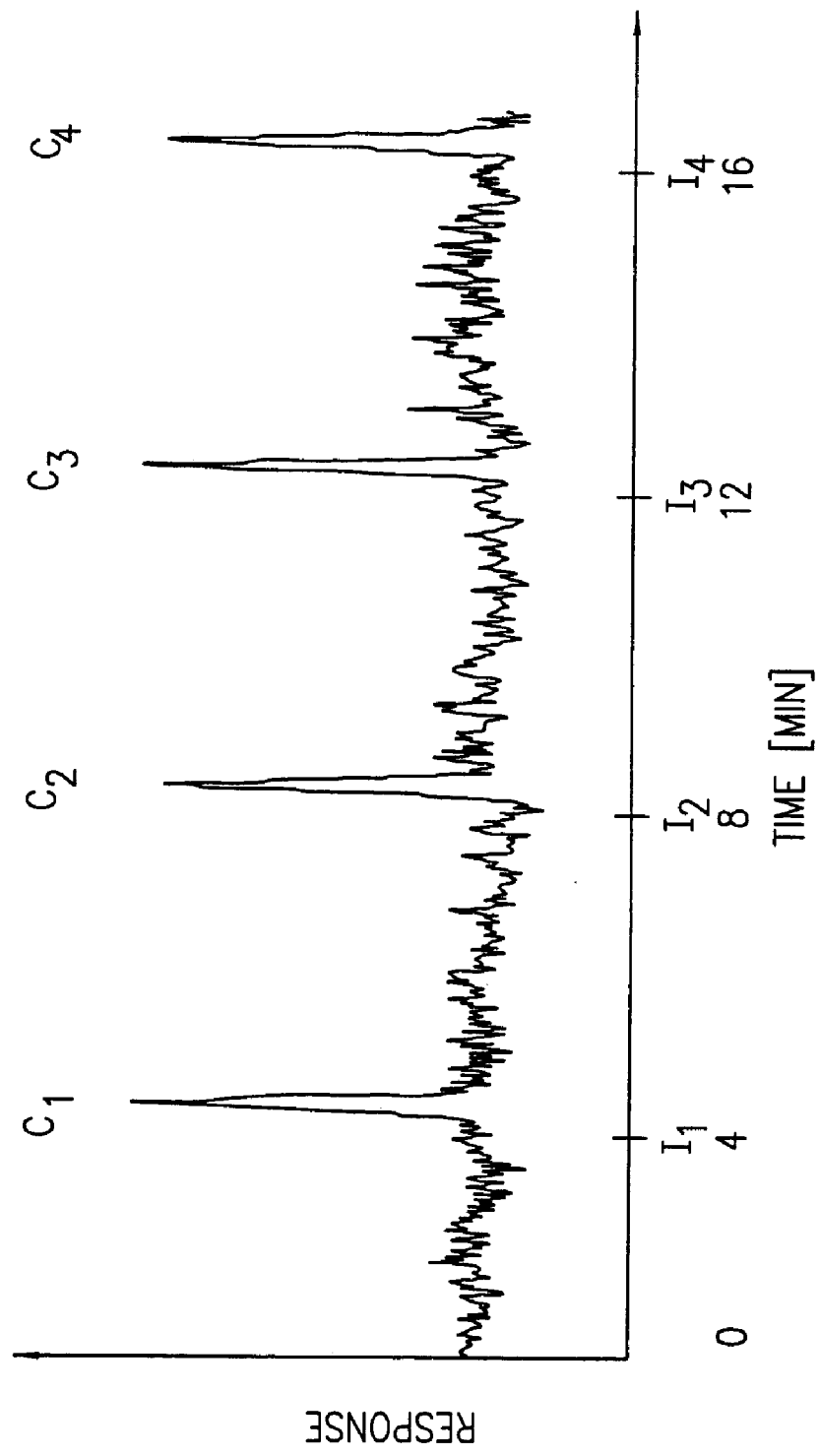
FIG. 7 is a graphical representation of analytical results reflecting continuous monitoring of a stream containing organics using a microconcentrator according to the present invention.

Now referring to FIG. 7, a microconcentrator according to the present invention was put on-line with the sample stream. The gaseous sample containing the analyte was introduced into the detector through the microconcentrator. The analytes were trapped in the polymer film 29 and could be thermally desorbed by electrical heating. The desorption was achieved by resistive heating by a current pulse (1 to 3 sec.). Rapid desorption was essential for producing a sharp concentration pulse to provide high throughput in terms of mass of sample per second. The mode of operation for continuous monitoring was that electrical pulses (injections "I") were made at fixed intervals of time, and corresponding to each injection, a signal pulse ("C") was obtained. Continuous monitoring using the microconcentrator 2 was demonstrated by monitoring a stream of organic vapors. As seen in FIG. 7, the microconcentrator 2 generated a series of signal pulses corresponding to a sequence of injections. The peaks represent a signal enhancement by a factor of fourteen, i.e., the signal from the microconcentrator 2 was fourteen times that obtained by direct sample introduction. Reproducibility in terms of peak height was excellent, and injection pulses could be continued indefinitely. The relative standard deviation in peak height based on six repeat injections was 1.02%.

Both adsorption and desorption processes played important roles in the on-line microconcentrator 2 operation. The adsorption capacity in terms of analyte breakthrough, and the desorption efficiency are important parameters. Because of its small dimensions, only a small mass of the sorbing phase 29 could be coated inside. Consequently, the microconcentrator 2 had inherently low capacity and was prone to breakthrough.

Figure 8:
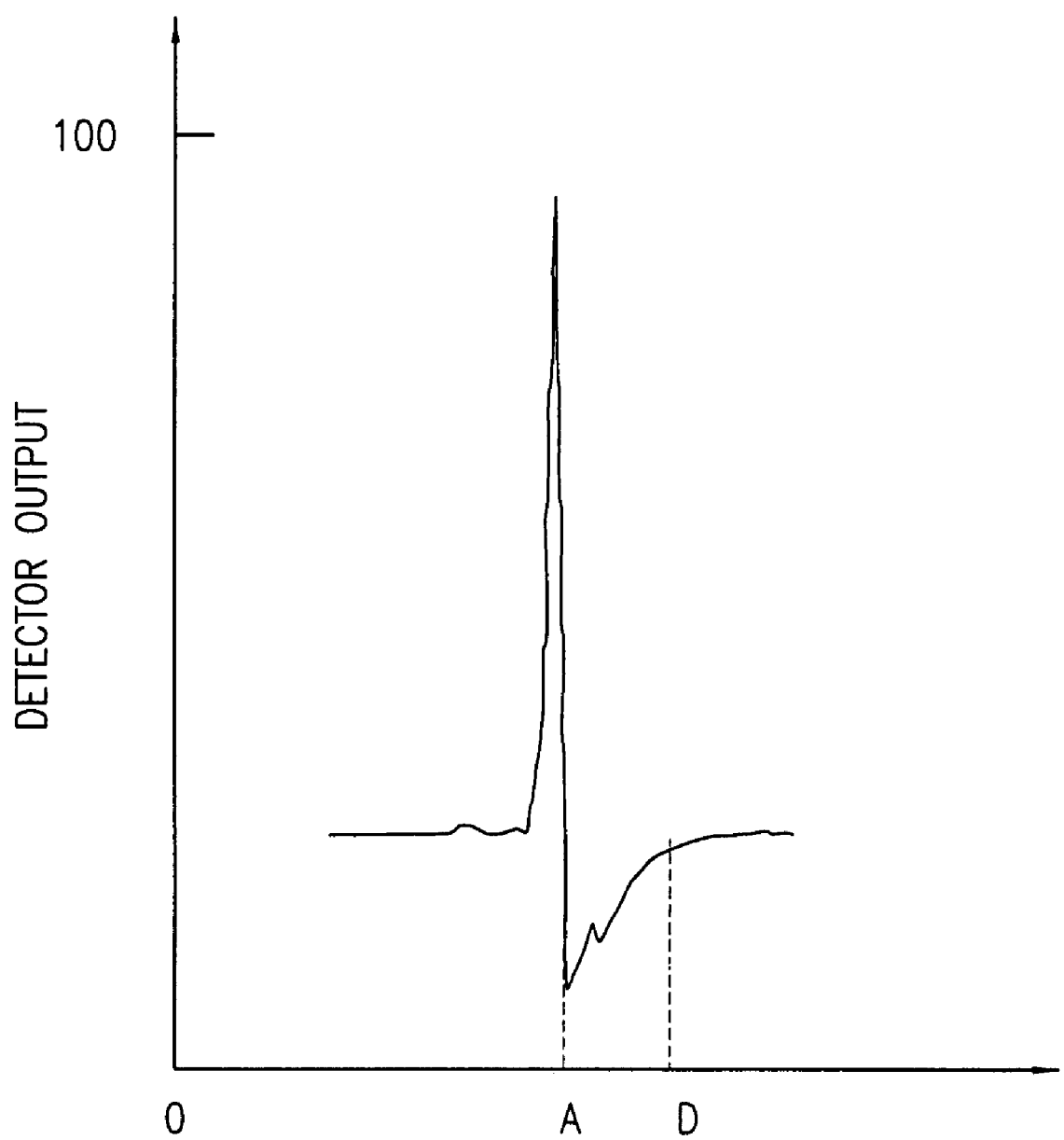
FIG. 8 is a graphical representation of a characteristic peak from a low capacity microconcentrator.

The breakthrough characteristics could be studied from the peak shape. The sample flowed continuously through the microconcentrator 2. When the microconcentrator 2 was heated, a desorption peak was observed. The analytes were re-adsorbed in the microconcentrator 2 as it cooled. This lowered the base line into the negative territory appearing as a negative peak. As the sample began to breakthrough, the detector response increased back to the base line. The width of the negative peak has been shown to equal to the breakthrough time, $t_b$, measured by frontal chromatography. The desorption generated a positive concentration profile while the immediate sample readsorption generated a negative one. Thus, a microconcentrator peak contained a positive and a negative part as shown in FIG. 8. The time interval AD in FIG. 8 is the time taken by the sample to migrate through the microconcentrator 2. This is denoted as:

$$t_b=(k+1)L/u \quad [1]$$

where L is the length of the microconcentrator 2, u is the linear velocity of the sample and k is the capacity factor of the sample in the microconcentrator 2 stationary phase. The capacity factor could be increased by using a stronger sorbing phase, or, by operating at a lower temperature. As the capacity factor increased, $t_b$ increased, the negative peak became drawn out and appeared to merge with the baseline. So, the remaining positive peak resembled a conventional concentration spike without a negative profile. FIG. 8 represents a low capacity microtrap with a relatively thin-film coating (0.7 μm) where the negative peak is pronounced, whereas, FIG. 7 shows the response of a higher capacity microconcentrator with a thicker polymer film (2.4 μm) and without the negative profile. A microconcentrator 2 with a higher capacity factor allowed longer breakthrough time, and generated peaks without the negative parts.

Experiment 3

Figure 9:
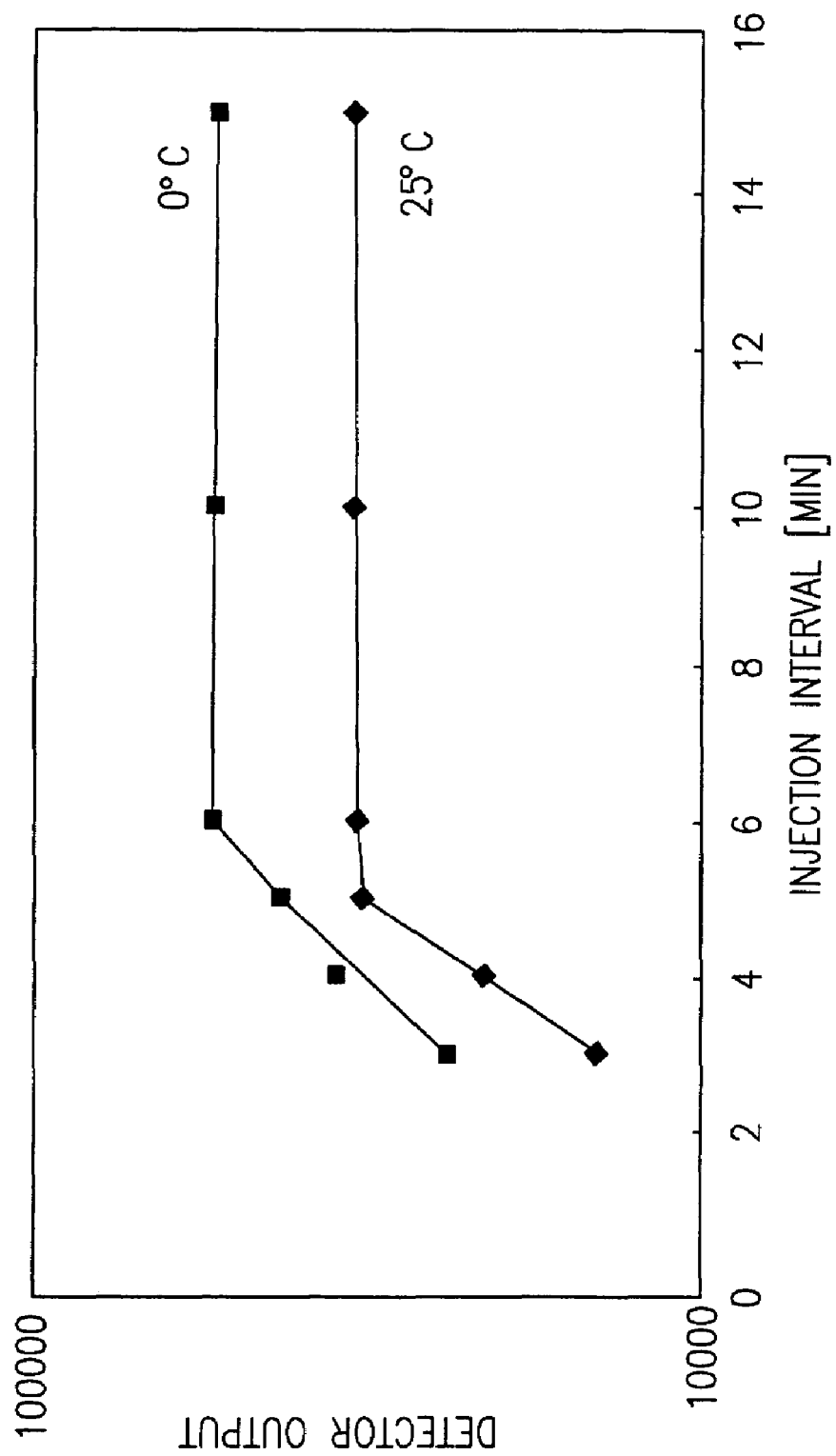
FIG. 9 is a graphical representation of analytical results reflecting the response of a microconcentrator according to the present invention as a function of injection interval at 0° C. and 25° C. employing toluene as the analyte.

Now referring to FIG. 9, the microconcentrator 2 response as a function of injection interval was studied at 0 and 25 C using toluene as the analyte. As the interval increased, the amount of sample trapped in the microconcentrator 2 increased. However, once the interval equaled $t_b$, the sample began to breakthrough, and the response could not be increased further. The response profile showed a linear increase in response up to $t_b$, followed by a constant response beyond $t_b$. It was seen that the temperature affected microconcentrator 2 operations; lower temperature increase $t_b$.

Linearity in microconcentrator response was observed as a function of concentration. The concentration range studied here was from 20 to 800 ppm of toluene. Since the amount of sample trapped in the microconcentrator was proportional to the concentration of the stream flowing in, its response was proportional to sample concentration. At a longer injection interval, the larger amount of trapped sample resulted in a higher response. The microconcentrator could be operated at any injection interval, either longer or shorter than $t_b$. Once beyond $t_b$, the sensitivity of the calibration curve did not increase with injection interval. Operating it at higher frequency resulted in faster monitoring, but allowed less time for sample accumulation, thus, lower sensitivity.

Experiment 4—Microconcentrator as a GC Injector

Figure 10:
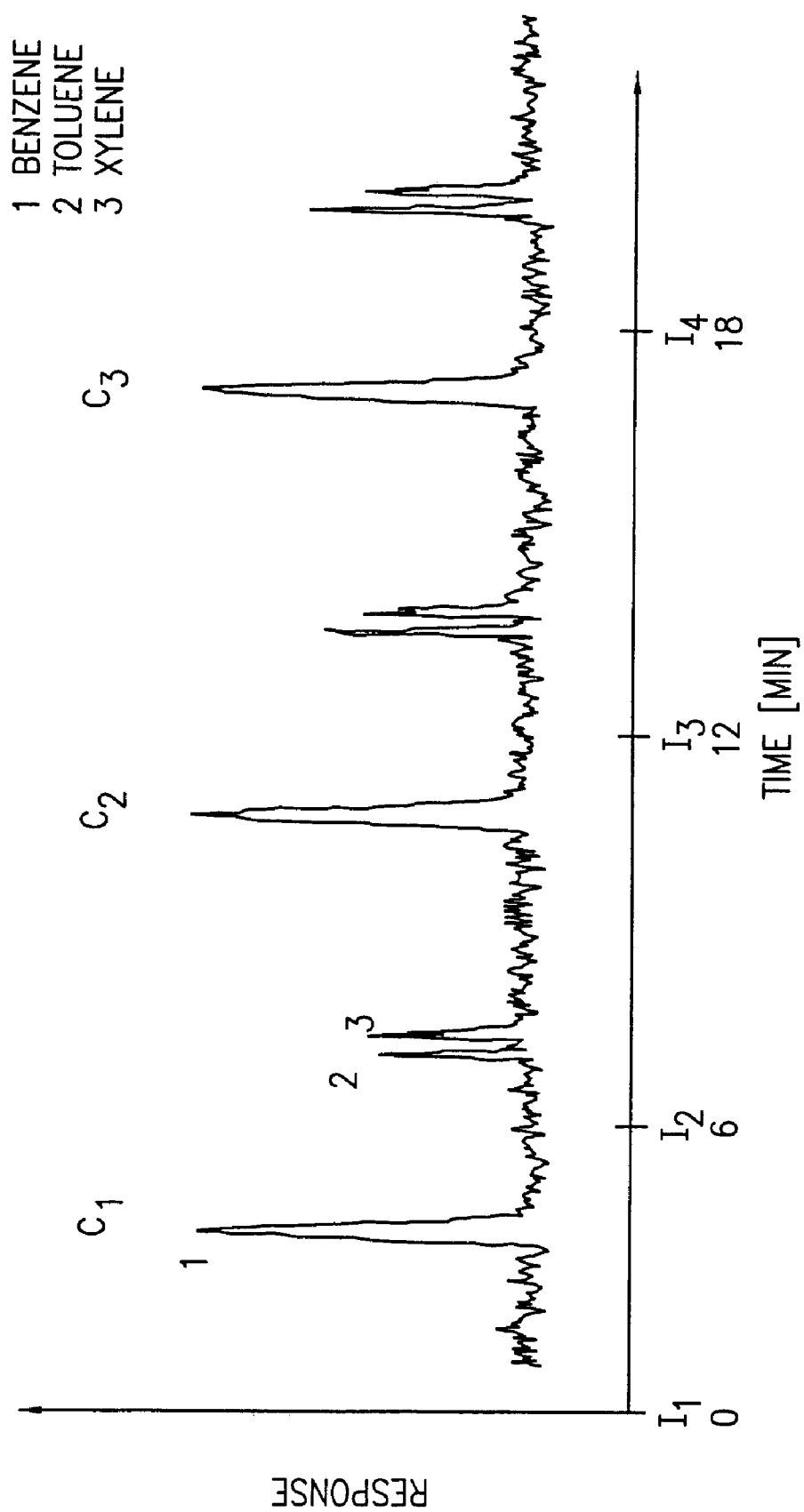
FIG. 10 is a graphical representation of analytical results reflecting continuous monitoring of a stream containing ppm levels of benzene, toluene and xylene using a microconcentrator according to the present invention.

Now referring to FIG. 10, a microconcentrator 2 in accordance with the present invention was also used as a GC injector. A mixture of benzene, toluene and xylene was used as the sample stream. A short megabore column was used for the separation of these compounds. A series of injections were made, and a chromatogram was obtained corresponding to each injection. Sharp peaks comparable to a conventional injection port were observed. This demonstrated that the injection band was narrow due to the rapid desorption from the microconcentrator 2. Reproducibility of retention time and peak height were very good. The relative standard deviation in peak height was consistently between 2 to 5%. The detection limit is dependent on the detector and could be lowered using a more sensitive laboratory instrument.

Microconcentrators according to the present invention were found to be rugged and could be operated practically indefinitely, showing no deterioration in performance over a year of laboratory operation.

While the preferred embodiments have been described and illustrated it will be understood that changes in details and obvious undisclosed variations might be made without departing from the spirit and principle of the invention and therefore the scope of the invention is not to be construed as limited to the preferred embodiment.

What is claimed is:

1. A microconcentrator comprising at least one microchannel formed on a substrate, at least one heating element in contact with at least one surface of the microchannel, and at least one absorbing layer disposed in said microchannel wherein analytes are sorbed on said absorbing layer and desorbed by application of heat from said heating element.

2. A microconcentrator according to claim 1 said heating element comprising a resistive layer selected from the group consisting of metal, metal alloys, composites of organic conducting polymers and metals and organic conducting polymers and implanted ions.

3. A microconcentrator according to claim 1 said absorbing layer is selected from the group consisting of polymer film, sorbent materials and carbon based sorbents.

4. A microconcentrator according to claim 1 said absorbing layer comprising gas chromatography stationary phase.

5. A microconcentrator according to claim 1 said substrate comprising silicon.

6. A microconcentrator according to claim 1 said substrate comprising glass or quartz.

7. A microconcentrator according to claim 1 said substrate comprising a polymer.

8. A microconcentrator according to claim 1 said substrate comprising an oriented, boron doped, single side polished silicon wafer.

9. A microconcentrator according to claim 1 further comprising a sealing layer disposed over said microchannel.

10. A microconcentrator according to claim 9 said sealing layer comprising a second microchannel comprising a mirror image of the first microchannel disposed over said first microchannel.

11. A microconcentrator according to claim 2 further comprising a further layer disposed on said resistive layer, said further layer selected from the group consisting of polymers, ceramics and glass.

12. A microconcentrator comprising a microchannel, said microchannel further comprising a microheater, said microheater comprising a resistive layer contacting at least an interior surface of said microchannel, said microconcentrator further comprising a sealing layer formed over said microchannel and an absorbing layer formed between said resistive layer and said sealing layer.

13. The device according to claim 12 said resistive layer selected from the group consisting of metal, metal alloys, composites of organic conducting polymers and metals, organic conducting polymers and implantated ions.

14. The device according to claim 12 said microchannel comprising a channel formed on a substrate said substrate selected from the group consisting of silicon, quartz, borosilicate wafers, and polymers.

15. A device according to claim 12 further comprising a glass layer disposed on said resistive layer.

16. A method for fabricating a microconcentrator comprising the steps of:

providing a substrate;

patterning said substrate;

forming a microchannel in said substrate;
forming a resistive layer in contact with at least an interior surface of said microchannel;
forming an absorbent layer in said microchannel; and
forming a sealing layer over said microchannel.

17. The method according to claim 16, said step of forming said microchannel comprising etching said substrate.

18. The method according to claim 16, said step of forming said resistive layer comprising ion implantation.

19. The method according to claim 18, said ion implantation step comprising implanting in said microchannel boron.

20. The method according to claim 16, said step of forming said resistive layer comprising forming a metal, metal alloy, organic conducting polymer or polymer-metal composite in said microchannel.

21. The method according to claim 16 said step of forming said resistive layer comprising sputtering aluminum or an alloy thereof in said microchannel.

22. The method according to claim 16 comprising the further step of applying a layer of glass over said resistive layer.

23. A device comprising a microconcentrator according to claim 1 and a sensor formed on said substrate.

24. The device according to claim 23 further comprising a micropump.

25. The device according to claim 23 further comprising a gas chromatography separator.

26. The device according to claim 23 said substrate comprising a single silicon wafer.

27. The device according to claim 1 comprising a gas chromatograph injector.

28. A microconcentrator comprising a microchannel comprising an interior surface, a heating element in contact with at least the interior surface of the microchannel, a sealing layer formed over said heating element and an absorbing layer formed between said heating element and said sealing layer.

29. A sensitivity enhancer for a sensor, a sensor array, detector or gas chromatograph comprising a microconcentrator according to claim 1.

30. An injector for sensors, sensor arrays, detectors and gas chromatographs comprising a microconcentrator according to claim 1.

31. A modulator in two dimensional gas chromatography and comprehensive two dimensional gas chromatography comprising a microconcentrator according to claim 1.

* * * * *